United States Patent
Bayer et al.

(10) Patent No.: US 6,169,056 B1
(45) Date of Patent: *Jan. 2, 2001

(54) HARMFUL FUNGI CONTROL WITH AN ACTIVE SUBSTANCE INHIBITING RESPIRATION BY INHIBITING THE CYTOCHROME COMPLEX III, COMBINED WITH AN AMIDE

(75) Inventors: Herbert Bayer; Hubert Sauter, both of Mannheim; Harald Köhle, Bobenheim; Günter Retzlaff, Römerberg; Eberhard Ammermann, Heppenheim; Gisela Lorenz, Hambach; Siegfried Strathmann, Limburgerhof; Karl Eicken, Wachenheim, all of (DE)

(73) Assignee: BASF Aktiengesellschaft, Ludwigshafen (DE)

( * ) Notice: Under 35 U.S.C. 154(b), the term of this patent shall be extended for 0 days.

This patent is subject to a terminal disclaimer.

(21) Appl. No.: 09/043,513

(22) PCT Filed: Sep. 23, 1996

(86) PCT No.: PCT/EP96/04151

§ 371 Date: Mar. 23, 1998

§ 102(e) Date: Mar. 23, 1998

(87) PCT Pub. No.: WO97/10716

PCT Pub. Date: Mar. 27, 1997

(30) Foreign Application Priority Data

Sep. 22, 1995 (DE) .............................. 195 35 366

(51) Int. Cl.[7] .................... A01N 63/00; A01N 43/40; A01N 43/72; A01N 43/36; A01N 43/02
(52) U.S. Cl. .................... 504/118; 504/130; 504/131; 504/132; 504/138; 504/140; 514/222.2; 514/228.2; 514/297; 514/272
(58) Field of Search .................... 504/118, 130, 504/131, 132, 138, 140; 514/222.2, 228.2, 297, 272

(56) References Cited

U.S. PATENT DOCUMENTS

| 4,829,085 | 5/1989 | Wenderoth et al. | 514/522 |
|---|---|---|---|
| 5,223,526 | 6/1993 | McLouglin et al. | 514/406 |
| 5,330,995 | 7/1994 | Eicken et al. | 514/355 |
| 5,438,070 | 8/1995 | Eicken et al. | 514/403 |
| 5,556,880 | 9/1996 | Latorse | 514/491 |

FOREIGN PATENT DOCUMENTS

| 9529834 | * 2/1996 | (AU) . |
| 254426 | 1/1988 | (EP) . |
| 382375 | 8/1990 | (EP) . |
| 394631 | 10/1990 | (EP) . |
| 741970 | 11/1996 | (EP) . |
| 95/15083 | 6/1995 | (WO) . |
| 96/03047 | 2/1996 | (WO) . |

OTHER PUBLICATIONS

Brandt et al., *Dechema monograph*, vol. 129, pp. 27–38, VCH, 1993.
Clough, *Natural Product Reports*, 1993, pp. 565–574.
Kohle et al., *Biochem. Soc. Trans.*, vol. 22, p. 635, 1993.
Buchenauer, *Chemistry of Plant Protection*, 1990, pp. 240–247.
*Chem. Abst.*, vol. 124, No. 3, 1996.
Ogur, *Chem. Abst.*, No. 124:281986, XP 002025269 (JP 08026911; Jan. 30, 1996).
Sumo, Derwent Abst., AN 95–224069 (WO 95/15083).
Farb, Derwent Abst., AN 95–237114 (JP7145012; Jun. 6, 1995).
Sumo, Derwent Abst., AN 96–074693 (JP 7330516; Dec. 19, 1995).
*Research Disclosure*, Jun. 1992, No. 338, pp. 506–510.

* cited by examiner

Primary Examiner—Jose' G. Dees
Assistant Examiner—Alton Pryor
(74) Attorney, Agent, or Firm—Keil & Weinkauf

(57) ABSTRACT

Compositions for controlling harmful fungi which comprise, as active ingredients, at least one compound which inhibits respiration on the cytochrome complex III and at least one amide compound of the formula II

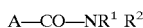

$$A—CO—NR^1 R^2$$

where A, $R^1$ and $R^2$ have the meanings given in the description. The compositions according to the invention can be used, in particular, for controlling botrytis.

11 Claims, No Drawings

HARMFUL FUNGI CONTROL WITH AN ACTIVE SUBSTANCE INHIBITING RESPIRATION BY INHIBITING THE CYTOCHROME COMPLEX III, COMBINED WITH AN AMIDE

This appln is a 371 of PCT/EP96/04151 filed Sep. 23, 1996.

The present invention relates to compositions for controlling harmful fungi and to methods of controlling harmful fungi using such compositions.

It is known from the literature that active ingredients which inhibit the cytochrome $bc_1$ complex (cytochrome complex III) can be employed as fungicides [cf. U. Brandt, U. Haase, H. Schägger, G. von Jagow: "Spezifität and Wirkmechanismus der Strobilurine" [Specificity and mechanism of action of the strobilurins], Dechema monograph Vol. 129, 27–38, VCH Verlagsgesellschaft Weinheim, 1993; J. M. Clough: Natural Product Reports, 1993, 565–574; F. R öhl, H. Sauter: Biochem. Soc. Trans. 22, 635 (1993)].

However, when using these active ingredients, it has emerged that their action is only transitory, ie. new fungal growth was observed after only a short time.

EP-A-545 099 describes anilide compounds of the formula

A—CO—NH—[phenyl substituted with R]

where A is phenyl which is substituted in the 2-position by methyl, trifluoromethyl, chlorine, bromine or iodine, or is one of certain aromatic or non-aromatic heterocyclic radicals which can be unsubstituted or substituted by methyl, chlorine or trifluoromethyl, and R is one of certain aliphatic or cycloaliphatic radicals which can be unsubstituted or substituted by halogen, or is phenyl which is unsubstituted or substituted by $C_1$–$C_4$-alkyl, $C_1$–$C_4$-alkoxy, $C_1$–$C_4$-alkylthio or halogen. These compounds can be used for controlling botrytis.

EP-A-589 301 describes anilide compounds of the same formula where A is a cyclic radical of the formulae:

[ring structures with $R^1_n$, $R^2$, $CH_3$, S, N, $H_2N$ substituents]

where $R^1$ is hydrogen or $C_1$–$C_4$-alkyl; $R^2$ is halogen or $C_1$–$C_4$-alkyl;
$R^3$ is $C_1$–$C_4$-alkyl or $C_1$–$C_4$-haloalkyl; n is 1 or 2; and R has essentially the abovementioned meanings. These compounds can also be used for treating botrytis.

WO 93/11117 describes compounds of the formula

[pyrazole-phenyl amide structure with substituents $R_1$, $Q_a$, $R_3$, $R_4$, $R_5$, $R_6$, $R_7$, $R_2$, X]

where
Q is $C_1$–$C_3$-alkyl, $C_2$–$C_3$-alkenyl, $C_2$–$C_3$-alkynyl, —$(CH_2)_m$CH= or —$(CH_2)_m$—X—$CH_2)$m;
n is 0 or 1;
  each m independently of the other is 0, 1, 2 or 3;
  each X independently is O or S;
$R^1$ is one of certain alicyclic radicals;
$R^2$ is hydrogen, fluorinated methyl, methyl, ethyl, $C_2$–$C_6$-alkenyl, $C_3$–$C_6$-chloroalkyl, phenyl, alkylthioalkyl, alkoxyalkyl, haloalkylthioalkyl, haloalkoxyalkyl or hydroxyalkyl;
$R^3$ is halomethyl, halomethoxy, methyl, ethyl, halogen, cyano, methylthio, nitro, aminocarbonyl or aminocarbonylmethyl;
$R^4$ is hydrogen, halogen or methyl;
$R^5$, $R^6$ and $R^7$ in each case independently of one another are selected from amongst hydrogen, halogen, cyano, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_3$–$C_4$-cycloalkyl and halomethoxy. These compounds are fungicidally active.

However, it has emerged that the abovementioned anilide compounds do not have a sufficiently broad and satisfactory spectrum of action.

It is an object of the present invention to provide an improved possibility of controlling harmful fungi, in particular botrytis.

Surprisingly, we have found that this object is achieved by a composition which comprises an active ingredient which inhibits respiration on cytochrome complex III in combination with an amide compound of the abovementioned type.

The present invention therefore relates to compositions for controlling harmful fungi which comprise, in a solid or liquid carrier,
  a) at least one active ingredient I, which inhibits respiration on cytochrome complex III, and
  b) at least one amide compound of the formula II $$A—CO—NR^1—R^2 \quad \text{(II)}$$

where
  A is an aryl group or an aromatic or non-aromatic 5- or 6-membered heterocycle which has 1 to 3 hereto atoms selected from amongst O, N and S;
    it being possible for the aryl group or the heterocycle to be unsubstituted or to have 1, 2 or 3 substituents, independently of one another selected from amongst alkyl, halogen, $CHF_2$, $CF_3$, alkoxy, haloalkoxy, alkylthio, alkylsulfinyl and alkylsulfonyl;
  $R^1$ is a hydrogen atom, alkyl or alkoxy;
  $R^2$ is a phenyl or cycloalkyl group which is unsubstituted or has 1 to 3 substituents, independently of one another selected from amongst phenyl, alkenyl, alkynyl, alkenyloxy, alkynyloxy, cycloalkyl, cycloalkenyl, cycloalkyloxy and cycloalkenyloxy and which can additionally be substituted by 1 or more halogen atoms, it being possible for the aliphatic and cycloaliphatic radicals to be partially or fully halogenated and/or for the cycloaliphatic radicals to be substituted by 1 to 3 alkyl groups, and it being possible for the phenyl group, in turn, to have 1 to 5 halogen atoms and/or 1 to 3 substituents, independently of one another selected from amongst alkyl, haloalkyl, alkoxy, haloalkoxy, alkylthio and haloalkylthio, and it being possible for the amidic phenyl group to be fused to a saturated 5-membered ring which is unsubstituted or substituted by one or more alkyl groups and/or can have one hereto atom selected from amongst O and S, with the exception of the compound of the formula II where A is 2-chloropyridin-3-yl, $R^1$ is H and $R^2$ is

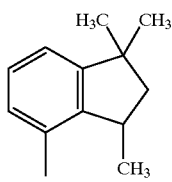

The compositions according to the invention have a synergistic action and are therefore especially suitable for controlling harmful fungi, in particular botrytis. It is assumed that this is based on the fact that, when respiration on the cytochrome complex III is inhibited, the fungus utilizes a secondary route of alternative respiration, so that the fungi are not destroyed completely. This would means that the amide compounds of the formula II inhibit the alternative respiration. It must therefore be assumed that the combination of the two active ingredients inhibits respiration via the cytochrome complex III and also the alternative respiration, so that the fungi are destroyed completely.

Halogen within the scope of the present invention is fluorine, chlorine, bromine and iodine, in particular fluorine, chlorine and bromine.

The term "alkyl" encompasses straight-chain or branched alkyl groups. They are preferably straight-chain or branched $C_1$–$C_{12}$-alkyl and, in particular, $C_1$–$C_6$-alkyl groups. Examples of alkyl groups are alkyl such as, in particular, methyl, ethyl, propyl, 1-methylethyl, butyl, 1-methylpropyl, 2-methylpropyl 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group as defined above which is partially or fully halogenated with one or more halogen atoms, in particular fluorine and chlorine. There are preferably 1 to 3 halogen atoms present, the difluoromethyl or the trifluoromethyl group being especially preferred.

What has been said above the alkyl group and haloalkyl group applies analogously to the alkyl and haloalkyl group in alkoxy, haloalkoxy, alkylthio, haloalkylthio, alkylsulfinyl, and alkylsulfonyl.

The alkenyl group encompasses straight-chain and branched alkenyl groups. Preferably, they are straight-chain or branched $C_3$–$C_{12}$-alkenyl groups, in particular $C_3$–$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group can be partially or fully halogenated with one or more halogen atoms, in particular fluorine and chlorine. Preferably, it has 1 to 3 halogen atoms.

The alkynyl group encompasses straight-chain and branched alkynyl groups. They are preferably straight-chain and branched $C_3$–$C_{12}$-alkynyl groups, in particular $C_3$–$C_6$-alkynyl groups.

Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl.

What has been said above about the alkenyl group and its halogen substituents, and about the alkynyl group, applies analogously to alkenyloxy and alkynyloxy.

The cycloalkyl group is preferably a $C_3$–$C_6$-cycloalkyl group, such as cyclopropyl, cyclobutyl, cyclopentyl or cyclohexyl. If the cycloalkyl group is substituted, it preferably has 1 to 3 $C_1$–$C_4$-alkyl radicals as substituents.

Cycloalkenyl is preferably a $C_4$–$C_6$-cycloalkenyl group, such as cyclobutenyl, cyclopentenyl or cyclohexenyl. If the cycloalkenyl group is substituted, it preferably has 1 to 3 $C_1$–$C_4$-alkyl radicals as substituents.

A cycloalkoxy group is preferably a $C_5$–$C_6$-cycloalkoxy group is such as cyclopentyloxy or cyclohexyloxy. If the cycloalkoxy group is substituted, it preferably has 1 to 3 $C_1$–$C_4$-alkyl radicals as substituents.

The cycloalkenyloxy group is preferably a $C_5$–$C_6$-cycloalkenyloxy group, such as cyclopentyloxy or cyclohexyloxy. If the cycloalkenyloxy group is substituted, it preferably has 1to 3 $C_1$–$C_4$-alkyl radicals as substituents.

Aryl is preferably phenyl.

Hetaryl is preferably a 5- or 6-membered aromatic heterocycle which has 1, 2 or 3 hetero atoms, independently of one another selected from amongst N, O and S. It is, in particular, pyridinyl, pyrimidinyl, thiazolyl, pyrazolyl, oxazolyl, isoxazol, isothiazolyl, imidazolyl, pyrrolyl, furanyl, thienyl or triazolyl.

Heterocyclyl is preferably a 5- or 6-membered saturated or unsaturated heterocycle which has 1, 2 or 3 hetero atoms, independently of one another selected from amongst N, O and S. It is, in particular, a dihydro, tetrahydro or hexahydro derivative of the radicals mentioned under "hetaryl". Pyrrolidinyl, tetrahydrofuranyl, imidazolidinyl, pyrazolidinyl, oxazolidinyl, isoxazolidinyl, thiazolidinyl, isothiazolidinyl, piperidinyl or morpholinyl are preferred.

If A in formula II is a phenyl group, it can have one, two or three of the abovementioned substituents in any position. Preferably, these substitutents, independently of one another, are selected from amongst alkyl, difluoromethyl, trifluoromethyl and halogen, in particular chlorine, bromine and iodine. Especially preferably, the phenyl group has a substituent in the 2-position.

If A is a 5-membered heterocycle, this is, in particular, a furyl, thiazolyl, pyrazolyl, imidazolyl oxazolyl, thienyl, triazolyl or thiadiazolyl radical or a corresponding dihydro or tetrahydro derivative thereof. A thiazolyl or pyrazolyl radical is preferred.

If A is a 6-membered heterocycle, this is, in particular, a pyridyl radical or a radical of the formula:

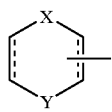

where one of the residues X and Y is O, S or $NR^9$, with $R^9$ being H or alkyl and the other one of residues X and Y being $CH_2$, S, SO, $SO_2$ or $NR^9$. The dotted line means that a double bond may, or may not, be present.

The 6-membered aromatic heterocycle is especially preferably a pyridyl radical, in particular a 3-pyridyl radical, or a radical of the formula (A3)

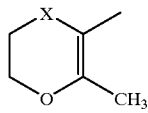

where X is $CH_2$, S, SO or $SO_2$.

The abovementioned heterocyclic radicals may be unsubstituted or have 1, 2 or 3 of the abovementioned substituents, these substituents, preferably, independently of one another being selected from amongst alkyl, halogen, difluoromethyl or trifluoromethyl.

A especially preferably is a radical of the formulae:

(A1)

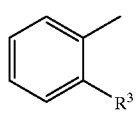

(A2)

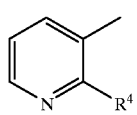

-continued (A5)

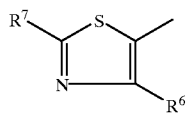

(A7)

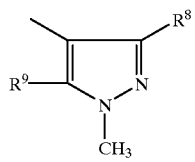

where $R^3$, $R^4$, $R^6$, $R^7$, $R^8$ and $R^9$ independently of one another are hydrogen, alkyl, in particular methyl, halogen, in particular chlorine, $CHF_2$ or $CF_3$.

The radical $R^1$ in formula II is preferably a hydrogen atom.

The radical $R^2$ in formula II is preferably a phenyl radical. $R^2$ preferably has at least one substituent, particularly preferably in the 2-position. The substituent (or substituents) is/are preferably selected from amongst alkyl, cycloalkyl, cycloalkenyl, halogen or phenyl.

The substituents of the radical $R^2$ can, in turn, also be substituted. The aliphatic or cycloaliphatic substituents can be partially or fully halogenated, in particular fluorinated or chlorinated. They preferably have 1, 2 or 3 fluorine or chlorine atoms. If the substituent of the radical $R^2$ is a phenyl group, it can preferably be substituted by 1 to 3 halogen atoms, in particular chlorine atoms and/or by a radical which is preferably selected from amongst alkyl and alkoxy Especially preferably, the phenyl group is substituted in the p-position with a halogen atom, ie. the especially preferred substituent of the radical $R^2$ is a p-halogen-substituted phenyl radical. The radical $R^2$ can also be fused to a saturated 5-membered ring, it being possible for this ring, in turn, to have 1 to 3 alkyl substituents. In this case, $R^2$ is, for example, indanyl, thiaindanyl and oxaindanyl. Preferred are indanyl and 2-oxaindanyl, which are bonded to the nitrogen atom in particular via the 4-position.

The active ingredient I is preferably a compound of the formula IA or IB:

IA

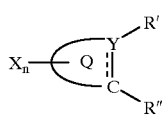

IB

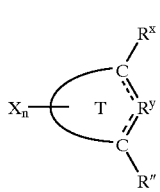

where ... is a double or single bond;

R' is —C[CO$_2$CH$_3$]═CHOCH$_3$, —C[CO$_2$CH$_3$]═NOCH$_3$, —C[CONHCH$_3$]═NOCH$_3$, —C[CO$_2$CH$_3$]═CHCH$_3$, —C[CO$_2$CH$_3$]═CHCH$_2$CH$_3$, —C[COCH$_3$]═NOCH$_3$, —C[COCH$_2$CH$_3$]═NOCH$_3$, —N(OCH$_3$)—CO$_2$CH$_3$, —N(CH$_3$)—CO$_2$CH$_3$ or —N(CH$_2$CH$_3$)—CO$_2$CH$_3$;

R" is an organic radical which is bonded directly or via an oxy, mercapto, amino, or alkylamino group, or together with a group X and the ring Q or T to which they are bonded an unsubstituted or substituted bicyclic, partially or fully unsaturated system which, besides carbon ring members, may contain 1, 2 or 3 hetero atoms, independently selected from amongst oxygen, sulfur and nitrogen;

$R^x$ is —OC[$CO_2CH_3$]=CHOCH$_3$, —OC[$CO_2CH_3$]=CHCH$_3$, —OC[$CO_2CH_3$]=CHCH$_2$CH$_3$, —SC[$CO_2CH_3$]=CHOCH$_3$, —SC[$CO_2CH_3$]=CHCH$_3$, —SC[$CO_2CH_3$]=CHCH$_2$CH$_3$, —N(CH$_3$)C[$CO_2CH_3$]=CHOCH$_3$, —N(CH$_3$)C[$CO_2CH_3$]=NOCH$_3$, —CH$_2$C[$CO_2CH_3$]=CHOCH$_3$, —CH$_2$C[$CO_2CH_3$]=NOCH$_3$ or —CH$_2$C[CONHCH$_3$]=NOCH$_3$;

$R^y$ is oxygen, sulfur, =CH— or =N—;

n is 0, 1, 2 or 3, it is possible for the radicals X to be identical or different if n>1;

X is cyano, nitro, halogen, alkyl, haloalkyl, alkoxy, haloalkoxy, alkylthio, or,
  if n>1, a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkylene, oxy-$C_2$–$C_4$-alkenyleneoxy or butadienediyl group bonded to two adjacent C atoms of the phenyl ring, it being possible for these chains, in turn, to have attached to them one to three radicals, independently of one another selected from amongst halogen, alkyl, haloalkyl, alkoxy, haloalkoxy and alkylthio;

Y is =C— or —N—;

Q is phenyl, pyrrolyl, thienyl, furyl, pyrazolyl, imidazolyl, oxazolyl, isoxazolyl, thiazolyl, thiadiazolyl, triazolyl, pyridinyl, 2-pyridonyl, pyrimidinyl or triazinyl; and T is phenyl, oxazolyl, thiazolyl, thiadiazolyl, oxadiazolyl, pyridinyl, pyrimidinyl or triazinyl.

The substituent R" is, in particular, an alkyl, alkenyl, alkynyl, aryl, hetaryl, arylalkyl, hetarylalkyl, arylalkenyl, hetarylalkenyl, arylalkynyl or hetarylalkynyl radical which is uninterrupted or interrupted by one or more groups selected from amongst O, S, SO, SO$_2$, NR (R=H or alkyl), CO, COO, OCO, CONH, NHCO and NHCONH, or a radical of the formula CH$_2$ON=CRαCRβ or CH$_2$ON=CRγCRδ=NORε defined below. These radicals are unsubstituted or have one or more (preferably 1, 2 or 3), substituents, independently of one another selected from amongst alkyl, alkoxy, halogen, cyano, haloalkyl (in particular CF$_3$ and CHF$_2$), hetaryl and aryl. Hetaryl, and aryl can, in turn, have 1, 2 or 3 substituents which, independently of one another, are selected from amongst halogen, haloalkyl (in particular CF$_3$ and CHF$_2$), phenyl, CN, phenoxy, alkyl, alkoxy and haloalkoxy.

Such compounds and their preparation are described in the literature given in Tables I.1 to I.8 below. Compounds not described therein can be prepared by similar methods.

In a preferred embodiment, the compositions according to the invention, comprise a compound of the formula IA or IB where R" is aryloxy, hetaryloxy, aryloxymethylene, hetaryloxymethylene, arylethenylene or hetarylethenylene, these radicals being unsubstituted or having 1, 2 or 3 substituents, independently of one another selected from amongst alkyl, halogen, CF$_3$, CHF$_2$, CN, alkoxy and phenyl which, in turn, can have 1, 2 or 3 substituents, independently of one another selected from amongst halogen, CF$_3$, CHF$_2$, phenyl, CN, phenoxy, alkyl, alkoxy and haloalkoxy; or R" is CH$_2$ON=CRαRβ or CH$_2$ON=CRγCRδ=NORε where
  Rα is alkyl;
  Rβ is phenyl, pyridyl or pyrimidyl, unsubstituted or having 1, 2 or 3 substituents independently of one another selected from amongst alkyl, alkoxy, halogen, haloalkoxy, CF$_3$ and CHF$_2$;
  Rγ is alkyl, alkoxy, halogen, haloalkyl or hydrogen;
  Rδ is hydrogen, cyano, halogen, alkyl, alkoxy, alkylthio, alkylamino, dialkylamino, alkenyl, alkenyloxy, alkenylthio, alkenylamino, N-alkenyl-N-alkylamino, alkynyl, alkynyloxy, alkynylthio, alkynylamino, N-alkynyl-N-alkylamino, it being possible for the hydrocarbon radicals of these groups to be partially or fully halogenated and/or to have attached to them 1, 2 or 3 radicals, independently selected from amongst cyano, nitro, hydroxyl, alkoxy, haloalkoxy, alkoxycarbonyl, alkylthio, alkylamino, dialkylamino, alkenyloxy, cycloalkyl, cycloalkyloxy, heterocyclyl, heterocyclyloxy, aryl, aryloxy, arylalkoxy, hetaryl, hetaryloxy and hetarylalkoxy, it being possible for the cyclic radicals, in turn, to be partially or fully halogenated and/or to have attached to them 1, 2 or 3 groups, independently selected from amongst cyano, nitro, hydroxyl, alkyl, haloalkyl, cycloalkyl, alkoxy, haloalkoxy, alkoxycarbonyl, alkylthio, alkylamino, dialkylamino, alkenyl and alkenyloxy;

or is cycloalkyl, cycloalkyloxy, cycloalkylthio, cycloalkylamino, N-cycloalkyl-N-alkylamino, heterocyclyl, heterocyclyloxy, heterocyclylthio, heterocyclylamino, N-heterocyclyl-N-alkylamino, aryl, aryloxy, arylthio, arylamino, N-aryl-N-alkylamino, hetaryl, hetaryloxy, hetarylthio, hetarylamino or N-hetaryl-N-alkylamino, it being possible for the cyclic radicals to be partially or fully halogenated and/or to have attached to them 1, 2 or 3 groups, independently selected from amongst cyano, nitro, hydroxyl, alkyl, haloalkyl, cycloalkyl, alkoxy, haloalkoxy, alkoxycarbonyl, alkylthio, alkylamino, dialkylamino, alkenyl, alkenyloxy, benzyl, benzyloxy, aryl, aryloxy, hetaryl and hetaryloxy, it being possible for the aromatic radicals, in turn, to be partially or fully halogenated and/or to have attached to them 1, 2 or 3 of the following groups: cyano, alkyl, haloalkyl, alkoxy, nitro;

Rε is alkyl, alkenyl or alkynyl, it being possible for these groups to be partially or fully halogenated and/or to have attached to them 1, 2 or 3 of the following radicals: cyano, alkoxy, cycloalkyl.

Especially preferred are compounds of the formula IA or IB where R" has one of the following meanings:

a) phenyloxymethylene, pyridinyloxymethylene, pyrimidinyloxymethylene or pyrazolyloxymethylene, the aromatic radical being unsubstituted or having 1, 2 or 3 substituents, independently of one another selected from amongst alkyl, halogen, CF$_3$, CHF$_2$, —C(CH$_3$)=NOCH$_3$, and phenyl which is unsubstituted or substituted by 1, 2 or 3 halogen atoms and/or alkyl groups;

b) phenoxy or pyrimidinyloxy, unsubstituted or substituted by 1, 2 or 3 halogen atoms or a phenoxy radical which is unsubstituted or has a halogen or cyano substituent;

c) phenylethenylene or pyrazolylethenylene, it being possible for the phenyl or pyrazolyl radical to be unsubstituted or to have 1, 2 or 3 substituents, independently of one another selected from amongst halogen, CF$_3$, CHF$_2$ and phenyl.

d) $CH_2ON{=}CR\alpha R\beta$ where $R\alpha$ is alkyl; and $R\beta$ is phenyl which is unsubstituted or has 1, 2 or 3 substituents, independently of one another selected from amongst alkyl, halogen, $CF_3$ and $CHF_2$, or is pyrimidinyl which is unsubstituted or is substituted by 1 or 2 alkoxy radicals;

e) $CH_2ON{=}CR\gamma CR\delta{=}NOR\epsilon$ where $R\gamma$ is alkyl, alkoxy or halogen;

$R\delta$ is alkyl, cyano, halogen, alkoxy, alkenyl or phenyl which is unsubstituted or is substituted by 1, 2 or 3 halogen atoms; and $R\epsilon$ is alkyl.

Particularly preferred are compounds of the formula IA where Q is phenyl and n is 0.

Especially suitable active ingredients I are compiled in the Tables which follow.

TABLE I.1A

Compounds of the formula IA where Q is phenyl, R' is —$C(CO_2CH_3){=}CHOCH_3$, n has a value of 0, R" is unsubstituted or substituted (het)aryloxymethylene, the unsubstituted or substituted (het)aryl group having the following meaning

| No. | Unsubst. or subst. (het)aryl | Literature |
|---|---|---|
| I.1A-1 | 2-$CH_3$—$C_6H_4$ | EP-A 226 917 |
| I.1A-2 | 2,5-$(CH_3)_2$—$C_6H_3$ | EP-A 226 917 |
| I.1A-3 | 2-$CH_3$, 4-C[$CH_3$]=$NOCH_3$—$C_6H_3$ | EP-A 386 561 |
| I.1A-4 | 2-$CH_2CH_2CH_3$, 6-$CF_3$-pyrimidin-4-yl | EP-A 407 873 |
| I.1A-5 | 2,4-$(CH_3)_2$—$C_6H_3$ | EP-A 226 917 |

TABLE I.1B

Compounds of the formula IA where R' is —$C(CO_2CH_3){=}CHOCH_3$, Q is phenyl, n has a value of 0, R" is unsubstituted or substituted (het)aryloxy, the unsubstituted or substituted (het)aryl group having the following meaning

| No. | Unsubst. or subst. (het)aryl | Literature |
|---|---|---|
| I.1B-1 | $C_6H_5$ | EP-A 178 826 |
| I.1B-2 | 6-[2-CN—$C_6H_4$—O]-pyrimidin-4-yl | EP-A 382 375 |

TABLE I.1C

Compounds of the formula IA where R' is —$C(CO_2CH_3){=}CHOCH_3$, Q is phenyl, n has a value of 0, R" is unsubstituted or substituted (het)arylethenylene, the unsubstituted or substituted (het)aryl group having the following meaning

| No. | Unsubst. or subst. (het)aryl | Literature |
|---|---|---|
| I.1C-1 | 1-(2,4-$Cl_2$—$C_6H_3$), 5-$CF_3$-pyrazol-4-yl | EP-A 528 245 |
| I.1C-2 | 1-(4-Cl—$C_6H_4$)-pyrazol-4-yl | EP-A 378 755 |
| I.1C-3 | 3-$CF_3$—$C_6H_4$ | EP-A 203 606 |
| I.1C-4 | 3-Cl—$C_6H_4$ | EP-A 203 606 |
| I.1C-5 | 4-$C_6H_5$—$C_6H_4$ | EP-A 203 606 |

TABLE I.1D

Compounds of the formula IA where Q is phenyl, R' is —$C(CO_2CH_3){=}CHOCH_3$, n has a value of 0, R" is $CH_2ON{=}CR\alpha R\beta$, $R\alpha$ and $R\beta$ having the following meanings

| No. | $R\alpha$ | $R\beta$ | Literature |
|---|---|---|---|
| I.1D-1 | $CH_3$ | 4-Cl—$C_6H_4$ | EP-A 370 629 |
| I.1D-2 | $CH_3$ | 3-$CF_3$—$C_6H_4$ | EP-A 370 629 |
| I.1D-3 | $CH_3$ | 4-$OCH_2CH_3$-pyrimidin-2-yl | WO-A 92/18,487 |

TABLE I.1E

Compounds of the formula IA where Q is phenyl, R' is —$C(CO_2CH_3){=}CHOCH_3$, n has a value of 0, R" is $CH_2ON{=}CR\gamma CR\delta{=}NOR\epsilon$, $R\gamma$, $R\delta$ and $R\epsilon$ having the following meanings

| No. | $R\gamma$ | $R\delta$ | $R\epsilon$ | Literature |
|---|---|---|---|---|
| I.1E-1 | $CH_3$ | $CH_3$ | $CH_3$ | WO-A 95/21153 |
| I.1E-2 | $CH_3$ | $CH_3$ | $CH_2CH_3$ | WO-A 95/21153 |
| I.1E-3 | $CH_3$ | $C_6H_5$ | $CH_3$ | WO-A 95/21153 |
| I.1E-4 | $CH_3$ | $C_6H_5$ | $CH_2CH_3$ | WO-A 95/21153 |
| I.1E-5 | $CH_3$ | 4-Cl—$C_6H_4$ | $CH_3$ | WO-A 95/21153 |
| I.1E-6 | $CH_3$ | 4-Cl—$C_6H_4$ | $CH_2CH_3$ | WO-A 95/21153 |

TABLE I.2A

Compounds of the formula IA where Q is phenyl, R' is —$C(CO_2CH_3){=}NOCH_3$, n has a value of 0, R" is unsubstituted or substituted (het)aryloxymethylene, the unsubstituted or substituted (het)aryl group having the following meaning

| No. | Unsubst. or subst. (het)aryl | Literature |
|---|---|---|
| I.2A-1 | 2-$CH_3$—$C_6H_4$ | EP-A 253 213 |
| I.2A-2 | 2,5-$(CH_3)_2$—$C_6H_3$ | EP-A 400 417 |
| I.2A-3 | 2,4-$(CH_3)_2$—$C_6H_3$ | EP-A 400 417 |
| I.2A-4 | 2,3,5-$(CH_3)_3$—$C_6H_2$ | EP-A 400 417 |
| I.2A-5 | 2-Cl, 5-$CH_3$—$C_6H_3$ | EP-A 400 417 |
| I.1A-6 | 2-$CH_3$, 4-C[$CH_3$]=$NOCH_3$—$C_6H_3$ | EP-A 386 561 |

TABLE I.2B

Compounds of the formula IA where Q is phenyl, R' is —$C(CO_2CH_3){=}NOCH_3$, n has a value of 0, R" is unsubstituted or substituted (het)aryloxy, the unsubstituted or substituted (het)aryl group having the following meaning

| No. | Unsubst. or subst. (het)aryl | Literature |
|---|---|---|
| I.2B-1 | $C_6H_5$ | EP-A 253 213 |
| I.2B-2 | 6-[2-CN—$C_6H_4$—O]-pyrimidin-4-yl | EP-A 468 684 |

TABLE I.2C

Compounds of the formula IA where Q is phenyl, R' is —$C(CO_2CH_3){=}NOCH_3$, n has a value of 0, R" is $CH_2ON{=}CR\alpha R\beta$, $R\alpha$ and $R\beta$ having the following meanings

| No. | $R\alpha$ | $R\beta$ | Literature |
|---|---|---|---|
| I.2C-1 | $CH_3$ | 4-Cl—$C_6H_4$ | EP-A 463 488 |
| I.2C-2 | $CH_3$ | 3-Cl—$C_6H_4$ | EP-A 463 488 |
| I.2C-3 | $CH_3$ | 4-$CF_3$—$C_6H_4$ | EP-A 463 488 |
| I.2C-4 | $CH_3$ | 3-$CF_3$—$C_6H_4$ | EP-A 463 488 |
| I.2C-5 | $CH_3$ | 4-$CH_3$—$C_6H_4$ | EP-A 463 488 |
| I.2C-6 | $CH_3$ | 4-$OCH_2CH_3$-pyrimidin-2-yl | EP-A 472 300 |

TABLE I.2C-continued

Compounds of the formula IA where Q is phenyl,
R' is —C(CO$_2$CH$_3$)=NOCH$_3$, n has a value of 0, R" is
CH$_2$ON=CRαRβ, Rα and Rβ
having the following meanings

| No. | Rα | Rβ | Literature |
|---|---|---|---|
| I.2C-7 | CH$_3$ | 3,5-Cl$_2$—C$_6$H$_3$ | EP-A 463 488 |

TABLE I.2D

Compounds of the formula IA where Q is phenyl,
R' is —C(CO$_2$CH$_3$)=NOCH$_3$, n has a value of 0, R" is
CH$_2$ON=CRγCRδ=NORε, Rγ,
Rδ and Rε having the following meanings

| No. | Rγ | Rδ | Rε | Literature |
|---|---|---|---|---|
| I.2D-1 | CH$_3$ | CH$_3$ | CH$_3$ | WO-A 95/21153 |
| I.2D-2 | CH$_3$ | CH$_3$ | CH$_2$CH$_3$ | WO-A 95/21153 |
| I.2D-3 | CH$_3$ | C$_6$H$_5$ | CH$_3$ | WO-A 95/21153 |
| I.2D-4 | CH$_3$ | C$_6$H$_5$ | CH$_2$CH$_3$ | WO-A 95/21153 |
| I.2D-5 | CH$_3$ | 4-Cl—C$_6$H$_4$ | CH$_3$ | WO-A 95/21153 |
| I.2D-6 | CH$_3$ | 4-Cl—C$_6$H$_4$ | CH$_2$CH$_3$ | WO-A 95/21153 |

TABLE I.3A

Compounds of the formula IA where Q is phenyl, R' is
—C(CONHCH$_3$)=NOCH$_3$, n has a value of 0, R" is unsubstituted
or substituted (het)aryloxymethylene, the unsubstituted or substituted
(het)aryl group having the following meaning

| No. | Unsubst. or subst. (het)aryl | Literature |
|---|---|---|
| I.3A-1 | 2-CH$_3$—C$_6$H$_4$ | EP-A 477 631 |
| I.3A-2 | 2,5-(CH$_3$)$_2$—C$_6$H$_3$ | EP-A 477 631 |
| I.3A-3 | 2,4-(CH$_3$)$_2$—C$_6$H$_3$ | EP-A 477 631 |
| I.3A-4 | 2,3,5-(CH$_3$)$_3$—C$_6$H$_2$ | EP-A 477 631 |
| I.3A-5 | 2-CH$_3$, 4-C[CH$_3$]=NOCH$_3$—C$_6$H$_3$ | EP-A 579 124 |
| I.3A-6 | 1-[4-Cl—C$_6$H$_4$]-pyrazol-3-yl | WO-A 94/19331 |
| I.3A-7 | 1-[2,4-Cl$_2$—C$_6$H$_3$]-pyrazol-3-yl | WO-A 94/19331 |

TABLE I.3B

Compounds of the formula IA where Q is phenyl, R' is
—C(CONHCH$_3$)=NOCH$_3$, n has a value of 0, R" is unsubstituted
or substituted (het)aryloxy, the unsubstituted or substituted
(het)aryl group having the following meaning

| No. | Unsubst. or subst. (het)aryl | Literature |
|---|---|---|
| I.3B-1 | C$_6$H$_5$ | EP-A 398 692 |
| I.3B-2 | 6-[2-CN—C$_6$H$_4$—O]-pyrimidin-4-yl | GB-A 2 253 624 |

TABLE I.3C

Compounds of the formula IA where Q is phenyl, R' is
—C(CONHCH$_3$)=NOCH$_3$, n has a value of 0, R" is unsubstituted
or substituted (het)aryloxymethylene, the unsubstituted or substituted
(het)aryl group having the following meaning

| No. | Unsubst. or subst. (het)aryl | Literature |
|---|---|---|
| I.3C-1 | 1-[2,4-Cl$_2$—C$_6$H$_3$], 5-CF$_3$-pyrazol-4-yl | DE-A 44 23 615.8 |

TABLE I.3D

Compounds of the formula IA where Q is phenyl,
R' is —C(CONHCH$_3$)=NOCH$_3$, n has a value of 0, R" is
CH$_2$ON=CRαRβ, Rα and Rβ
having the following meanings

| No. | Rα | Rβ | Literature |
|---|---|---|---|
| I.3D-1 | CH$_3$ | 4-Cl—C$_6$H$_4$ | EP-A 463 488 |
| I.3D-2 | CH$_3$ | 3-Cl$_3$—C$_6$H$_4$ | EP-A 463 488 |
| I.3D-3 | CH$_3$ | 4-CF$_3$—C$_6$H$_4$ | EP-A 585 751 |
| I.3D-4 | CH$_3$ | 3-CF$_3$—C$_6$H$_4$ | EP-A 585 751 |
| I.3D-5 | CH$_3$ | 4-CH$_3$—C$_6$H$_4$ | EP-A 463 488 |
| I.3D-6 | CH$_3$ | 3,5-Cl$_2$—C$_6$H$_3$ | EP-A 463 488 |
| I.3D-7 | CH$_3$ | 2-OCH$_2$CH$_3$-pyrimidin-2-yl | WO-A 92/13,830 |

TABLE I.3E

Compounds of the formula IA where Q is phenyl,
R' is —C(CONHCH$_3$)=NOCH$_3$, n has a value of 0, R" is
CH$_2$ON=CRγCRδ=NORε, Rγ,
Rδ and Rε having the following meanings

| No. | Rγ | Rδ | Rε | Literature |
|---|---|---|---|---|
| I.3E-1 | CH$_3$ | CH$_3$ | CH$_3$ | WO-A 95/21154 |
| I.3E-2 | CH$_3$ | CH$_3$ | CH$_2$CH$_3$ | WO-A 95/21154 |
| I.3E-3 | CH$_3$ | C$_6$H$_5$ | CH$_3$ | WO-A 95/21154 |
| I.3E-4 | CH$_3$ | C$_6$H$_5$ | CH$_2$CH$_3$ | WO-A 95/21154 |
| I.3E-5 | CH$_3$ | 4-Cl—C$_6$H$_4$ | CH$_3$ | WO-A 95/21154 |
| I.3E-6 | CH$_3$ | 4-Cl—C$_6$H$_4$ | CH$_2$CH$_3$ | WO-A 95/21154 |
| I.3E-7 | CH$_3$ | 4-F—C$_6$H$_4$ | CH$_3$ | WO-A 95/21154 |

TABLE I.4A

Compounds of the formula IA where Q is phenyl, R' is
—C(CO$_2$CH$_3$)=CHCH$_3$, n has a value of 0, R" is unsubstituted
or substituted (het)aryloxymethylene, the unsubstituted or substituted
(het)aryl group having the following meaning

| No. | Unsubst. or subst. (het)aryl | Literature |
|---|---|---|
| I.4A-1 | 2-CH$_3$—C$_6$H$_4$ | EP-A 280 185 |
| I.4A-2 | 2,5-(CH$_3$)$_2$—C$_6$H$_3$ | EP-A 513 580 |
| I.4A-3 | 2,4-(CH$_3$)$_2$—C$_6$H$_3$ | EP-A 513 580 |
| I.4A-4 | 2,3,5-(CH$_3$)$_3$—C$_6$H$_2$ | EP-A 513 580 |
| I.4A-5 | 2-Cl, 5-CH$_3$—C$_6$H$_3$ | EP-A 513 580 |
| I.4A-6 | 2-CH$_3$, 4-C[CH$_3$]=NOCH$_3$—C$_6$H$_3$ | EP-A 513 580 |
| I.4A-7 | 1-[4-Cl—C$_6$H$_4$]-pyrazol-3-yl | DE-A 44 15 483.6 |

TABLE I.4B

Compounds of the formula IA where Q is phenyl, R' is
—C(CO$_2$CH$_3$)=CHCH$_3$, n has a value of 0, R" is unsubstituted
or substituted (het)aryloxy, the unsubstituted or substituted
(het)aryl group having the following meaning

| No. | Unsubst. or subst. (het)aryl | Literature |
|---|---|---|
| I.4B-1 | C$_6$H$_5$ | EP-A 513 580 |

TABLE I.4C

Compounds of the formula IA where Q is phenyl, R' is
—C(CO$_2$CH$_3$)=CHCH$_3$, n has a value of 0, R" is
CH$_2$ON=CRγCRδ=NORε, Rγ,
Rδ and Rε having the following meanings

| No. | Rγ | Rδ | Rε | Literature |
|---|---|---|---|---|
| I.4C-1 | CH$_3$ | CH$_3$ | CH$_3$ | WO-A 95/21153 |
| I.4C-2 | CH$_3$ | CH$_3$ | CH$_2$CH$_3$ | WO-A 95/21153 |
| I.4C-3 | CH$_3$ | C$_6$H$_5$ | CH$_3$ | WO-A 95/21153 |
| I.4C-4 | CH$_3$ | C$_6$H$_5$ | CH$_2$CH$_3$ | WO-A 95/21153 |
| I.4C-5 | CH$_3$ | 4-Cl—C$_6$H$_4$ | CH$_3$ | WO-A 95/21153 |
| I.4C-6 | CH$_3$ | 4-Cl—C$_6$H$_4$ | CH$_2$CH$_3$ | WO-A 95/21153 |

TABLE I.5A

Compounds of the formula IA where Q is phenyl, R' is
—C(CO$_2$CH$_3$)=CHCH$_2$CH$_3$, n has a value of 0, R" is unsubstituted
or substituted (het)aryloxymethylene, the unsubstituted or substituted
(het)aryl group having the following meaning

| No. | Unsubst. or subst. (het)aryl | Literature |
|---|---|---|
| I.5A-1 | 2-CH$_3$—C$_6$H$_4$ | EP-A 513 580 |
| I.5A-2 | 2,5-(CH$_3$)$_2$—C$_6$H$_3$ | EP-A 513 580 |
| I.5A-3 | 2,4-(CH$_3$)$_2$—C$_6$H$_3$ | EP-A 513 580 |
| I.5A-4 | 2,3,5-(CH$_3$)$_3$—C$_6$H$_2$ | EP-A 513 580 |
| I.5A-5 | 2-Cl, 5-CH$_3$—C$_6$H$_3$ | EP-A 513 580 |
| I.5A-6 | 2-CH$_3$, 4-C[CH$_3$]=NOCH$_3$—C$_6$H$_3$ | EP-A 513 580 |

TABLE I.5B

Compounds of the formula IA where Q is phenyl, R' is
—C(CO$_2$CH$_3$)=CHCH$_2$CH$_3$, n has a value of 0, R" is unsubstituted
or substituted (het)aryloxy, the unsubstituted or substituted
(het)aryl group having the following meaning

| No. | Unsubst. or subst. (het)aryl | Literature |
|---|---|---|
| I.5B-1 | C$_6$H$_5$ | EP-A 513 580 |

TABLE I.5C

Compounds of the formula IA where Q is phenyl,
R' is —C(CO$_2$CH$_3$)=CH$_2$CH$_3$, n has a value of 0, R" is
CH$_2$ON=CRγCRδ=NORε, Rγ,
Rδ and Rε having the following meanings

| No. | Rγ | Rδ | Rε | Literature |
|---|---|---|---|---|
| I.5C-1 | CH$_3$ | CH$_3$ | CH$_3$ | WO-A 95/21153 |
| I.5C-2 | CH$_3$ | CH$_3$ | CH$_2$CH$_3$ | WO-A 95/21153 |
| I.5C-3 | CH$_3$ | C$_6$H$_5$ | CH$_3$ | WO-A 95/21153 |
| I.5C-4 | CH$_3$ | C$_6$H$_5$ | CH$_2$CH$_3$ | WO-A 95/21153 |
| I.5C-5 | CH$_3$ | 4-Cl—C$_6$H$_4$ | CH$_3$ | WO-A 95/21153 |
| I.5C-6 | CH$_3$ | 4-Cl—C$_6$H$_4$ | CH$_2$CH$_3$ | WO-A 95/21153 |

TABLE I.6A

Compounds of the formula IA where Q is phenyl, R' is
—C(COCH$_3$)=NOCH$_3$, n has a value of 0, R" is unsubstituted
or substituted (het)aryloxymethylene, the unsubstituted or substituted
(het)aryl group having the following meaning

| No. | Unsubst. or subst. (het)aryl | Literature |
|---|---|---|
| I.6A-1 | 2-CH$_3$—C$_6$H$_4$ | EP-A 498 188 |
| I.6A-2 | 2,5-(CH$_3$)$_2$—C$_6$H$_3$ | EP-A 498 188 |
| I.6A-3 | 2,4-(CH$_3$)$_2$—C$_6$H$_3$ | EP-A 498 188 |
| I.6A-4 | 2,3,5-(CH$_3$)$_3$—C$_6$H$_2$ | EP-A 498 188 |
| I.6A-5 | 2-CH$_3$, 4-C[CH$_3$]=NOCH$_3$—C$_6$H$_3$ | EP-A 498 188 |

TABLE I.6B

Compounds of the formula IA where Q is phenyl, R' is
—C(COCH$_3$)=NOCH$_3$, n has a value of 0, R" is unsubstituted
or substituted (het)aryloxy, the unsubstituted or substituted
(het)aryl group having the following meaning

| No. | Unsubst. or subst. (het)aryl | Literature |
|---|---|---|
| I.6B-1 | C$_6$H$_5$ | EP-A 498 188 |
| I.6B-2 | 6-[2-CN—C$_6$H$_4$—O]-pyrimidin-4-yl | EP-A 498 188 |

TABLE I.7A

Compounds of the formula IA where Q is phenyl, R' is
—C(COCH$_2$CH$_3$)=NOCH$_3$, n has a value of 0, R" is unsubstituted
or substituted (het)aryloxymethylene, the unsubstituted or substituted
(het)aryl group having the following meaning

| No. | Unsubst. or subst. (het)aryl | Literature |
|---|---|---|
| I.7A-1 | 2-CH$_3$—C$_6$H$_4$ | EP-A 498 188 |
| I.7A-2 | 2,5-(CH$_3$)$_2$—C$_6$H$_3$ | EP-A 498 188 |
| I.7A-3 | 2,4-(CH$_3$)$_2$—C$_6$H$_3$ | EP-A 498 188 |
| I.7A-4 | 2,3,5-(CH$_3$)$_3$—C$_6$H$_2$ | EP-A 498 188 |
| I.7A-5 | 2-CH$_3$, 4-C[CH$_3$]=NOCH$_3$—C$_6$H$_3$ | EP-A 498 188 |

TABLE I.7B

Compounds of the formula IA where Q is phenyl, R' is
—C(COCH$_2$CH$_3$)=NOCH$_3$, n has a value of 0, R" is unsubstituted
or substituted (het)aryloxy, the unsubstituted or substituted
(het)aryl group having the following meaning

| No. | Unsubst. or subst. (het)aryl | Literature |
|---|---|---|
| I.7B-1 | C$_6$H$_5$ | EP-A 498 188 |
| I.7B-2 | 6-[2-CN—C$_6$H$_4$—O]-pyrimidin-4-yl | EP-A 498 188 |

TABLE I.8A

Compounds of the formula IA where Q is phenyl, R' is
—N(OCH$_3$)—CO$_2$CH$_3$, n has a value of 0, R" is unsubstituted
or substituted (het)aryloxymethylene, the unsubstituted or substituted
(het)aryl group having the following meaning

| No. | Unsubst. or subst. (het)aryl | Literature |
|---|---|---|
| I.8A-1 | 2-CH$_3$—C$_6$H$_4$ | WO-A 93/15,046 |
| I.8A-2 | 2,5-(CH$_3$)$_2$—C$_6$H$_3$ | WO-A 93/15,046 |
| I.8A-3 | 2,4-(CH$_3$)$_2$—C$_6$H$_3$ | WO-A 93/15,046 |
| I.8A-4 | 2,3,5-(CH$_3$)$_3$—C$_6$H$_2$ | WO-A 93/15,046 |
| I.8A-5 | 2-Cl, 5-CH$_3$—C$_6$H$_3$ | WO-A 93/15,046 |
| I.8A-6 | 2-CH$_3$, 4-C[CH$_3$]=NOCH$_3$—C$_6$H$_3$ | WO-A 93/15,046 |
| I.8A-7 | 2-CH$_3$, 4-C[CH$_3$]=NOCH$_2$CH$_3$—C$_6$H$_3$ | WO-A 93/15,046 |
| I.8A-8 | 2-CH$_3$, 4-C[CH$_2$CH$_3$]=NOCH$_3$—C$_6$H$_3$ | WO-A 93/15,046 |
| I.8A-9 | 2-CH$_3$, 4-C[CH$_2$CH$_3$]=NOCH$_2$CH$_3$—C$_6$H$_3$ | WO-A 93/15,046 |
| I.8A-10 | 1-[4-Cl—C$_6$H$_4$]-pyrazol-3-yl | DE-A 44 23 612.3 |

TABLE I.8B

Compounds of the formula IA where Q is phenyl,
R' is —N(OCH$_3$)=CO$_2$CH$_3$, n has a value of 0, R" is
CH$_2$ON=CR$\alpha$R$\beta$, R$\alpha$ and R$\beta$
having the following meanings

| No. | R$\alpha$ | R$\beta$ | Literature |
|---|---|---|---|
| I.8B-1 | CH$_3$ | 3,5-Cl$_2$—C$_6$H$_3$ | WO-A 93/15,046 |

In a further preferred embodiment, the composition according to the invention comprises, as the amide compound, a compound of the formula II where A has the following meanings: phenyl, pyridyl, dihydropyranyl, dihydrooxathiinyl, dihydrooxathiinyl oxide, dihydrooxathiinyl dioxide, furyl, thiazolyl, pyrazolyl or oxazolyl, it being possible for these groups to have 1, 2 or 3 substituents, independently of one another selected from amongst alkyl, halogen, difluoromethyl and trifluoromethyl.

In a further preferred embodiment, A represents: pyridin-3-yl which is unsubstituted or substituted in the 2-position by halogen, methyl, difluoromethyl, trifluoromethyl, methoxy, methylthio, methylsulfinyl or methylsulfonyl;

phenyl which is unsubstituted or substituted in the 2-position by methyl, trifluoromethyl, chlorine, bromine or iodine;

2-methyl-5,6-dihydropyran-3-yl;

2-methyl-5,6-dihydro-1,4-oxathiin-3-yl or the 4-oxide or 4,4-dioxide thereof;

2-methyl-furan-3-yl which is unsubstituted or substituted in the 4- and/or 5-position by methyl;

thiazol-5-yl which is unsubstituted or substituted in the 2- and/or 4-position by methyl, chlorine, difluoromethyl or trifluoromethyl;

thiazol-4-yl which is unsubstituted or substituted in the 2- and/or 5-position by methyl, chlorine, difluoromethyl or trifluoromethyl;

1-methylpyrazol-4-yl which is unsubstituted or substituted in the 3- and/or 5-position by methyl, chlorine, difluoromethyl or trifluoromethyl; or oxazol-5-yl which is unsubstituted or substituted in the 2- and/or 4-position by methyl or chlorine.

In a further preferred embodiment, the compositions according to the invention comprise, as the amide compound, a compound of the formula II where R$^2$ is a phenyl group which is unsubstituted or substituted by 1, 2 or 3 of the abovementioned substituents.

In a further preferred embodiment, the compositions according to the invention comprise, as the amide compound, a compound of the formula II where R$^2$ is a phenyl group which has one of the following substituents in the 2-position: C$_3$–C$_6$-alkyl, C$_5$–C$_6$-cycloalkenyl, C$_5$–C$_6$-cycloalkyloxy, C$_5$–C$_6$-cycloalkenyloxy, it being possible for these groups to be substituted by 1, 2 or 3 C$_1$–C$_4$-alkyl groups, phenyl which is substituted by 1 to 5 halogen atoms and/or 1 to 3 groups independently of one another selected from amongst C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio and C$_1$–C$_4$-haloalkylthio, indanyl or oxaindanyl, unsubstituted or substituted by 1, 2 or 3 C$_1$–C$_4$-alkyl groups.

In a further preferred embodiment, the compositions according to the invention comprise, as the amide compound, a compound of the formula IIa,

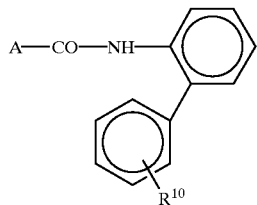
(IIa)

where A is

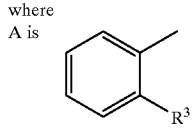
(A1)

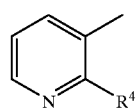
(A2)

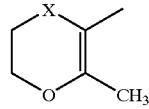
(A3)

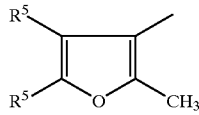
(A4)

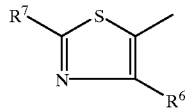
(A5)

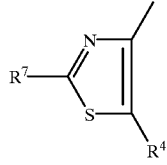
(A6)

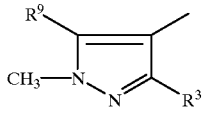
(A7)

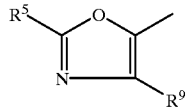
(A8)

X is methylene, sulfur, sulfinyl or sulfonyl (SO$_2$),

R$^3$ is methyl, difluoromethyl, trifluoromethyl, chlorine, bromine or iodine,

R$^4$ is trifluoromethyl or chlorine,

R$^5$ is hydrogen or methyl,

R$^6$ is methyl, difluoromethyl, trifluoromethyl or chlorine,

R$^7$ is hydrogen, methyl or chlorine,

R$^8$ is methyl, difluoromethyl or trifluoromethyl, $R^9$ is hydrogen, methyl, difluoromethyl, trifluoromethyl or chlorine, and $R^{10}$ is $C_1$–$C_4$-alkyl, $C_1$–$C_4$-alkoxy, $C_1$–$C_4$-alkylthio or halogen.

In an especially preferred embodiment, the compositions comprise, as the amide compound, a compound of the formula IIb

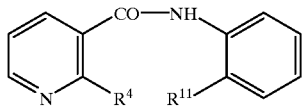

(IIb)

where $R^4$ is hydrogen and $R^{11}$ is phenyl which is substituted by halogen.

Suitable amide compounds are mentioned in EP-A-545 -099 and 589 301, which are herewith referred to in their entirety. The preparation of the amide compounds of the formula I is disclosed, for example, in EP-A-545 099 or 589 301 or can be carried out by similar processes.

To obtain the synergistic effect, the active ingredients are employed in a weight ratio in a range of from 20:1 to 1:20, in particular 10:1 to 1:10.

The invention also relates to a method of controlling harmful fungi, which comprises treating the fungi, their environment, or the materials, plants, seeds, soils, areas or spaces to be protected against fungal infection, with a composition as defined above, it being possible for the active ingredients to be applied simultaneously, ie. jointly or separately, or in succession.

The compositions according to the invention can be applied, for example, in the form of directly sprayable solutions, powders, suspensions, also highly-concentrated aqueous, oily or other suspensions or dispersions, emulsions, oil dispersions, pastes, dusts, materials for spreading or granules by means of spraying, atomizing, dusting, spreading or pouring. The use forms depend on the intended purposes; in any case, they should guarantee the finest possible distribution of the active ingredients according to the invention.

Normally, the plants are sprayed or dusted with the active ingredients, or the seeds of the plants are treated with the active ingredients.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and round synthetic minerals (eg. highly-dispersed silica, silicates); emulsifiers, such as non-ionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are the alkali metal, alkaline earth metal and ammonium salts of aromatic sulfonic acids, eg. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates; and salts of sulfated hexa-, hepta- and octadecanols, or else fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenyl ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Solid carriers are mineral earths, such as silica gel, silicas, silica gels, silicates, talc, kaolin, limestone, lime, chalk, bole, loess, clay, dolomite, diatomacious earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

Examples of such preparations which comprise the active ingredients in a weight ratio of 1:1 are:

I. a solution of 90 parts by weight of the active ingredients and 10 parts by weight of N-methylpyrrolidone which is suitable for use in the form of microdrops;

II. a mixture of 20 parts by weight of the active ingredients, 80 parts by weight of xylene, 10 parts by weight of the adduct of 8 to 10 mol of ethylene oxide to 1 mol of oleic acid N-monoethanolamide, 5 parts by weight of calcium dodecylbenzene-sulfonate, 5 parts by weight of the adduct of 40 mol of ethylene oxide to 1 mol of castor oil; a dispersion is obtained by finely distributing the solution in water;

III. an aqueous dispersion of 20 parts by weight of the active ingredients, 40 parts by weight of cyclohexanone, 30 parts by weight of isobutanol, 20 parts by weight of the adduct of 40 mol of ethylene oxide to 1 mol of castor oil;

IV. an aqueous dispersion of 20 parts by weight of the active ingredients, 25 parts by weight of cyclohexanol, 65 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight of the active ingredients, 3 parts by weight of sodium diisobutylnaphthalene-1-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of the active ingredients and 97 parts by weight of finely divided kaolin; this dust comprises 3% by weight of active ingredient;

VII. an intimate mixture of 30 parts by weight of the active ingredients, 92 parts by weight of pulverulent silica gel and 8 parts by weight of paraffin oil which had been sprayed onto the surface of this silica gel; this preparation imparts good adhesive properties to the active ingredient;

VIII. a stable aqueous dispersion of 40 parts by weight of the active ingredients, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of the active ingredients, 2 parts by weight of calcium dodecylbenzene-sulfonate, 8 parts by weight of fatty alcohol polyglycol ether, 20 parts by weight of the sodium salt of a phenolsulfonic acid/urea/formaldehyde condensate and 88 parts by weight of a paraffin mineral oil.

The compositions according to the invention are distinguished by an outstanding activity against a broad spectrum of phytopathogenic fungi, in particular against botrytis. some of them act systemically (ie. they can be taken up by the treated plants without losing their activity and, if appropriate, translocated within the plant) and can be employed as foliar- and soil-acting fungicides.

They are particularly important for controlling a large number of fungi in a variety of crop plants such as wheat, rye, barley, oats, rice, maize, grass, cotton, soybeans, coffee, sugar cane, grapevine, fruit species, ornamentals and vegetable species such as cucumbers, beans and cucurbits, and on the seeds of these plants.

The compositions are applied by treating the fungi, or the seeds, plants, materials or the soil to be protected against fungal infection, with a fungicidally active amount of the active ingredients.

Application is effected before or after infection of the materials, plants or seeds with the fungi.

Specifically, the compositions are suitable for controlling the following plant diseases:

Erysiphe graminis (powdery mildew) in cereals,
Erysiphe cichoracearum and Sphaerotheca fuliginea in cucurbits,
Podosphaera leucotricha in apples,
Uncinula necator in grapevines,
Venturia inaequalis (scab) in apples,
Helminthosporium species in cereals,
Septoria nodorum in wheat,
Botrytis cinerea (gray mold) in strawberries and grapevines,
Cercospora arachidicola in groundnuts,
Pseudocercosporella herpotrichoides in wheat and barley,
Pyricularia oryzae in rice,
Fusarium and Verticillium species in a variety of plants,
Alternaria species in vegetables and fruit,
Monilinia species in fruit,
Sclerotinia species in oilseed rape and vegetables.

The use against botrytis is preferred.

The compositions can also be employed in the protection of material (protection of wood), for example against Paecilomyces variotii.

In general, the fungicidal compositions comprise from 0.1 to 95, preferably 0.5 to 90, % by weight of active ingredient. Depending on the nature of the desired effect, the rates of application are from 0.02 to 3 kg of active ingredient per ha. In the treatment of seeds, amounts of from 0.001 to 50 g, preferably 0.01 to 10 g, of active ingredient are generally required per kilogram of seed.

In the use form as fungicides, the compositions according to the invention can also comprise other active ingredients, eg. herbicides, insecticides, growth regulators, fungicides or else fertilizers.

In many cases, a mixture with fungicides results in a widened fungicidal spectrum of action.

The following list of fungicides together with which the compounds according to the invention can be used is intended to illustrate the possible combinations, but not to impose any limitations:
sulfur,
dithiocarbonates and their derivatives, such as
iron(III) dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfide,
ammonia complex of zinc (N,N-ethylenebisdithiocarbamate),
ammonia complex of zinc (N,N'-propylenebisdithiocarbamate),
zinc (N,N'-propylenebisdithiocarbamate),
N,N'-polypropylenebis(thiocarbamoyl)disulfide,
nitro derivatives, such as
dinitro(1-methylheptyl)phenyl crotonate,
2-sec-butyl-4,6-dinitrophenyl 3,3-dimethylacrylate,
2-sec-butyl-4,6-dinitrophenylisopropyl carbonate,
diisopropyl 5-nitroisophthalate:
heterocyclic substances, such as
2-heptadecyl-2-imidazoline acetate,
2,4-dichloro-6-(o-chloroanilino)-s-triazine,
O,O-diethyl phthalimidophosphonothioate,
5-amino-1-[bis(dimethylamino)phosphinyl])-3-phenyl-1,2,4,-triazole,
2,3-dicyano-1,4-dithioanthraquinone,
2-thio-1,3-dithiolo[4,5-b]quinoxaline,
1-(butylcarbamoyl)-2-benzimidazolecarbamate,
2-methoxycarbonylaminobenzimidazole,
2-(furyl-(2))benzimidazole,
2-(thiazolyl-(4))benzimidazole,
N-(1,1,2,2-tetrachloroethylthio)tetrahydrophthalimide,
N-trichloromethylthiotetrahydrophthalimide,
N-trichloromethylthiophthalimide,
N-dichlorofluoromethylthio-N',N'-dimethyl-N-phenylsulfuramide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
pyridine-2-thiol 1-oxide,
8-hydroxyquinoline and its copper salt,
2,3-dihydro-5-carboxanilido-6-methyl-1,4-oxathiine,
2,3-dihydro-5-carboxanilido-6-methyl-1,4-oxathiine 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
N-cyclohexyl-2,5-dimethylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethyl acetate,
piperazine-1,4-diylbis(1-(2,2,2-trichloroethyl)formamide,
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert-butylphenyl)-2-methylpropyl]-cis-2,6-dimethylmorpholine,
N-[3-(p-tert-butylphenyl)-2-methylpropyl]piperidine,
1-[2-(2,4-dichlorophenyl)-4-ethyl-1,3-dioxolan-2-yl-ethyl]-1H-1,2,4-triazole
1-[2-(2,4-dichlorophenyl)-4-n-propyl)-1,3-dioxolan-2-yl-ethyl]-1H-1,2,4-triazole
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)-2-butanone, 1-(4-chlorophenyl)-3,3-dimethyl)-1-(1H-1,2,4-triazol-1-yl)-2-butanol,
α-(2-chlorophenyl)-α-(4-chlorophenyl)-5-pyrimidinemethanol,
5-butyl-2-dimethylamino-4-hydroxy-6-methylpyrimidine,
bis(p-chlorophenyl)-3-pyridinemethanol,
1,2-bis(3-ethyoxycarbonyl-2-thioureido)benzene,
1,2-bis(3-methoxycarbonyl-2-thioureido)benzene,
and a variety of fungicides, such as
dodecylguanidine acetate,
3-[3-(3,5-dimethyl)-2-oxycyclohexyl)-2-hydroxyethyl)]-glutarimide,
hexachlorobenzene,
DL-methyl-N-(2,6-dimethylphenyl)-N-(2-furoyl)alaninate,
DL-N-(2,6-dimethylphenyl)-N-(2'-methoxyacetyl)alanine methyl ester,
N-(2,6-dimethylphenyl)-N-chloroacetyl-D,L-2-aminobutyrolactone,
DL-N-(2,6-dimethylphenyl)-N-(phenylacetyl)alanine methyl ester,
5-methyl-5-vinyl-3-(3,5-dichlorophenyl)-2,4-dioxo-1,3-oxazolidine,
3-[3,5-dichlorophenyl-(5-methyl-5-methoxymethyl]-1,3-oxazolidine-2,4-dione,
3-(3,5-dichlorophenyl)-1-isopropylcarbamoylhydantoin,
N-(3,5-dichlorophenyl)-1,2-dimethylcyclopropane-1,2-dicarboximide,
2-cyano-[N-(ethylaminocarbonyl)-2-methoximino]acetamide,
1-[2-(2,4-dichlorophenyl)pentyl]-1H-1,2,4-triazole,
2,4-difluoro-α-(1H-1,2,4-triazolyl-1-methyl)benzhydryl alcohol,
N-(3-chloro-2,6-dinitro-4-trifluoromethylphenyl)-5-trifluoromethyl-3-chloro-2-aminopydridine,
1-((bis(4-fluorophenyl)methylsilyl)methyl-1H-1,2,4-triazole.

The synergistic action of the compositions according to the invention is illustrated with the aid of the Use Examples which follow, the active ingredients I which are employed being the compounds of the formulae I.1 to I5

I.1

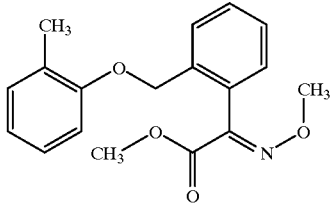

I.2

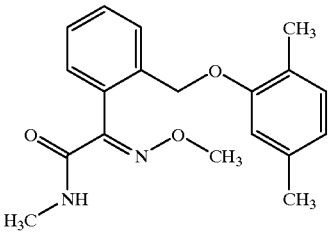

I.3

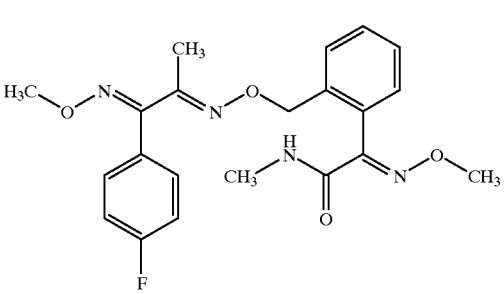

I.4

I.5 and the amide compounds employed being the compounds of the formulae II.b 1and II.2

II.1

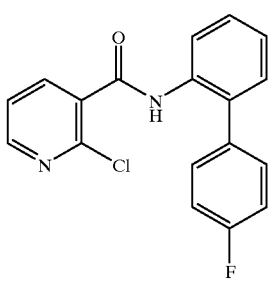

II.2

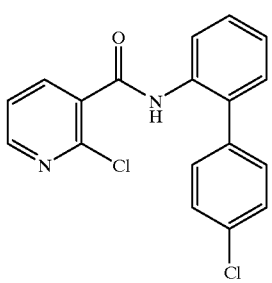

USE EXAMPLE 1

Activity against *Botrytis cinerae* on bell pepper fruits
Disks of green bell pepper fruits were sprayed to drip point with an aqueous preparation of the active ingredient comprising 80% of active ingredient and 20% of emulsifier in the dry matter. 2 hours after the spray coating had dried on, the fruit disks were inoculated with a spore suspension of Botrytis cinerea comprising 1.7×10⁶ spores per ml of a 2% strength Biomalz solution. The inoculated fruit disks were subsequently incubated for 4 days in humid chambers at 18° C. The botrytis development on the infected fruit disks was then evaluated visually (disease level 100%).

The visually determined values for the percentage of infected fruit area were converted into efficacies expressed in % of the untreated control. An efficacy of 0 is the same disease level as in the untreated control, an efficacy of 100 is a disease level of 0%. The expected efficacies for active ingredient combinations were determined using Colby's formula (Colby, S. R. (Calculating synergistic and antagonistic responses of herbicide Combinations", Weeds, 15, pp. 20–22, 1967) and compared with the observed efficacies. The results are shown in Table 1 below.

TABLE 1

| Active ingredient | Active ingredient concentration in ppm | | Efficacy in % of the control | |
|---|---|---|---|---|
| ingredient | I.1–I.3 | II.1 | Observed | Calculated* |
| Control (untreated) | — | — | 0 | — |
| II.I | 15 | | 50 | |
| | 7.5 | | 20 | |
| I.1 | 5 | | 25 | |
| | 2.5 | | 15 | |
| I.2 | 5 | | 20 | |
| | 2.5 | | 10 | |
| I.3 | 5 | | 5 | |
| | 2.5 | | 0 | |
| I.1 + II.1 | 5 | 15 | 99 | 62 |
| | 2.5 | 7.5 | 97 | 32 |
| I.2 + II.1 | 5 | 15 | 96 | 55 |
| I.3 + II.1 | 5 | 15 | 86 | 52 |
| | 2.5 | 7.5 | 60 | 20 |

*calculated using Colby's formula

The test results show that the efficacy observed in all mixing ratios exceeds the additive efficacy calculated beforehand using Colby's formula, ie. a synergistic effect is present.

USE EXAMPLE 2

Activity against Botrytis cinerea

After 4–5 leaves had developed properly, bell pepper seedlings cv. "Neusiedler Ideal Elite" were sprayed to drip point with aqueous suspensions comprising 80% of active ingredient and 20% of emulsifier in the dry matter. After the spray coating had dried on, the plants were sprayed with a conidia suspension of the fungus Botrytis cinerea and placed into a chamber at 22–24° C. and high atmospheric humidity. After 5 days, the untreated control plants had developed such an extent of the disease that the leaf necroses formed covered most of the leaves (disease level 96%).

The visually determined values for the percentage of infected leaf area were converted into efficacies expressed in % of the untreated control. An efficacy of 0 is the same disease level as in the untreated control, an efficacy of 100 is a disease level of 0%. The expected efficacies for active ingredient combinations were determined using Colby's formula (Colby, S. R. (Calculating synergistic and antagonistic responses of herbicide Combinations", Weeds, 15 pp. 20–22, 1967) and compared with the observed efficacies. The results are shown in Table 2 below.

TABLE 2

| Active ingredient | Active ingredient concentration in ppm | | Efficacy in % of the control | |
|---|---|---|---|---|
| ingredient | I.1–I.3 | II.1 | Observed | Calculated* |
| Control (untreated) | | | | |
| II.2 | — | 24 | 87 | — |
| | | 6 | 79 | |
| | | 1.5 | 28 | |
| I.1 | 2 | — | 0 | — |
| | 0.5 | | 0 | |
| I.2 | 2 | — | 0 | — |
| | 0.5 | | 0 | |
| I.3 | 2 | — | 0 | — |
| | 0.5 | | 0 | |
| I.4 | 2 | — | 0 | — |
| | 0.5 | | 0 | |
| I.5 | 2 | — | 0 | — |
| | 0.5 | | 0 | |
| I.1 + II.2 | 2 | 6 | 100 | 87 |
| | 0.5 | 1.5 | 100 | 79 |
| I.2 + II.2 | 2 | 6 | 100 | 87 |
| | 0.5 | 1.5 | 99 | 79 |
| I.3 + II.2 | 2 | 6 | 100 | 87 |
| | 0.5 | 1.5 | 99 | 79 |
| I.4 + II.2 | 2 | 6 | 100 | 87 |
| | 0.5 | 1.5 | 100 | 79 |
| I.5 + II.2 | 2 | 6 | 99 | 87 |
| | 0.5 | 1.5 | 90 | 79 |

*calculated using Colby's formula

The test results shown that the efficacy observed in all mixing ratios exceeds the additive efficacy calculated beforehand using Colby's formula, ie. a synergistic effect is present.

Similar results are obtained when the amide compound employed is one of the compounds of the formula Ia.

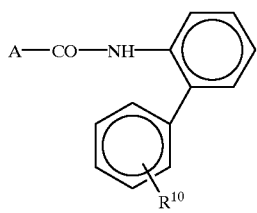

where A is

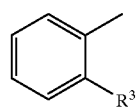
(A1)

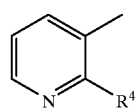
(A2)

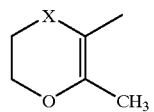
(A3)

-continued (A5)

(A7)

which are mentioned in Table 3 below, or another of the individual compounds mentioned in EP-A-545 099 and 589 301 and/or one of the individual compounds mentioned in the above Tables I.1 to I.8.

(I)

wherein

R' is —C[CO₂CH₃]=CHOCH₃, —C[CO₂CH₃]=NOCH₃, —C[CONHCH₃]=NOCH₃, —C[CO₂CH₃]=CHCH₃, —C[CO₂CH₃]=CHCH₂CH₃, —C[COCH₃]=NOCH₃, —C[COCH₂CH₃]=NOCH₃, —N(OCH₃)—CO₂CH₃, —N(CH₃)—CO₂CH₃ or —N(CH₂CH₃)—CO₂CH₃

R" has one of the following meanings:
  a) phenyloxymethylene, pyridinyloxymethylene, pyrimidinyloxymethylene or pyrazolyloxymethylene,

TABLE 3

| No. | A | $R^3$ | $R^4$ | $R^5$ | $R^6$ | $R^7$ | $R^8$ | $R^9$ | $R^{10}$ | X | Physical data (° C.) |
|---|---|---|---|---|---|---|---|---|---|---|---|
| 3.1 | $A_1$ | $CH_3$ | — | — | — | — | — | — | 2-F | — | |
| 3.2 | $A_1$ | $CH_3$ | — | — | — | — | — | — | 4-F | — | |
| 3.3 | $A_1$ | $CF_3$ | — | — | — | — | — | — | 2-F | — | |
| 3.4 | $A_1$ | $CF_3$ | — | — | — | — | — | — | 4-F | — | |
| 3.5 | $A_2$ | — | Cl | — | — | — | — | — | 2-F | — | |
| 3.6 | $A_2$ | — | Cl | — | — | — | — | — | 2-$CH_3$ | — | 71–73 |
| 3.7 | $A_2$ | — | Cl | — | — | — | — | — | 2-Cl | — | |
| 3.8 | $A_2$ | — | Cl | — | — | — | — | — | 2-$OCH_3$ | — | |
| 3.9 | $A_2$ | — | Cl | — | — | — | — | — | 3-F | — | |
| 3.10 | $A_2$ | — | Cl | — | — | — | — | — | 3-Cl | — | 95–98 |
| 3.11 | $A_2$ | — | Cl | — | — | — | — | — | 3-$CH_3$ | — | |
| 3.12 | $A_2$ | — | Cl | — | — | — | — | — | 3-$OCH_3$ | — | |
| 3.13 | $A_2$ | — | Cl | — | — | — | — | — | 3-$OiC_3H_7$ | — | |
| 3.14 | $A_2$ | — | Cl | — | — | — | — | — | 3-Br | — | |
| 3.15 | $A_2$ | — | Cl | — | — | — | — | — | 4-F | — | 156–157 |
| 3.16 | $A_2$ | — | Cl | — | — | — | — | — | 4-Cl | — | 142–144 |
| 3.17 | $A_2$ | — | Cl | — | — | — | — | — | 4-$CH_3$ | — | 115–117 |
| 3.18 | $A_2$ | — | Cl | — | — | — | — | — | 4-$OCH_3$ | — | 114–116 |
| 3.19 | $A_2$ | — | Cl | — | — | — | — | — | 4-$SCH_3$ | — | |
| 3.20 | $A_3$ | — | — | — | — | — | — | — | 2-F | $CH_2$ | |
| 3.21 | $A_3$ | — | — | — | — | — | — | — | 3-F | $CH_2$ | |
| 3.22 | $A_3$ | — | — | — | — | — | — | — | 4-F | $CH_2$ | |
| 3.23 | $A_3$ | — | — | — | — | — | — | — | 3-Cl | $CH_2$ | |
| 3.24 | $A_3$ | — | — | — | — | — | — | — | 3-$CH_3$ | $CH_2$ | |
| 3.25 | $A_3$ | — | — | — | — | — | — | — | 2-F | S | |
| 3.26 | $A_3$ | — | — | — | — | — | — | — | 3-F | S | |
| 3.27 | $A_3$ | — | — | — | — | — | — | — | 4-F | S | |
| 3.28 | $A_3$ | — | — | — | — | — | — | — | 3-Cl | S | |
| 3.29 | $A_3$ | — | — | — | — | — | — | — | 3-$CH_3$ | S | |
| 3.30 | $A_3$ | — | — | — | — | — | — | — | 2-F | $SO_2$ | |
| 3.31 | $A_3$ | — | — | — | — | — | — | — | 3-F | $SO_2$ | |
| 3.32 | $A_3$ | — | — | — | — | — | — | — | 4-F | $SO_2$ | |
| 3.33 | $A_3$ | — | — | — | — | — | — | — | 3-Cl | $SO_2$ | |
| 3.34 | $A_3$ | — | — | — | — | — | — | — | 3-$CH_3$ | $SO_2$ | |
| 3.35 | $A_5$ | — | — | — | $CF_3$ | $CH_3$ | — | — | 2-F | — | |
| 3.36 | $A_5$ | — | — | — | $CF_3$ | $CH_3$ | — | — | 3-F | — | |
| 3.37 | $A_5$ | — | — | — | $CF_3$ | $CH_3$ | — | — | 4-F | — | |
| 3.38 | $A_7$ | — | — | — | — | — | $CH_3$ | Cl | 2-F | — | |
| 3.39 | $A_7$ | — | — | — | — | — | $CH_3$ | Cl | 3-F | — | |
| 3.40 | $A_7$ | — | — | — | — | — | $CH_3$ | Cl | 4-F | — | |
| 3.41 | $A_7$ | — | — | — | — | — | $CF_3$ | Cl | 2-F | — | |
| 3.42 | $A_7$ | — | — | — | — | — | $CF_3$ | Cl | 4-F | — | |

We claim:

1. A composition for controlling harmful fungi comprising, in a solid or liquid carrier, A) at lease one active ingredient I, which inhibits respiration on cytochrome complex III, of the formula I the aromatic radical being unsubstituted or having 1, 2 or 3 substituents, independently of one another selected from the group consisting of alkyl, halogen, $CF_3$, $CHF_2$, —$(CH_3)$=$NOCH_3$, and phenyl which is unsubstituted or substituted by 1, 2 or 3 halogen atoms and/or alkyl groups;

b) phenoxy or pyrimidinyloxy, unsubstituted or substituted by 1, 2 or 3 halogen atoms or a phenoxy radical which is unsubstituted or has a halogen or cyano substituent;
c) $CH_2ON{=}CR^\alpha R^\beta$ where $R^\alpha$ is alkyl; and $R^\beta$ is phenyl which is unsubstituted or has 1, 2 or 3 substituents, independently of one another selected from the group consisting of alkyl, halogen, $CF_3$, $CHF_2$;
d) $CH_2ON{=}CR^\gamma CR^\delta{=}NOR^\epsilon$ where $R^\gamma$ is alkyl; $R^\delta$ is alkyl or phenyl which is unsubstituted or is substituted by 1, 2 or 3 halogen atoms; and $R^\epsilon$ is alkyl or alkenyl; and B) at least one amide compound of the formula II $$A\text{—}CO\text{—}NR^1\text{—}R^2 \qquad (II)$$

where

A is one of the following groups:

pyridiyl, thiazolyl, pyrazolyl or oxazolyl, it being possible for these groups to have 1, 2 or 3 substituents, independently of one another selected from the group consisting of alkyl, halogen, difluoromethyl, trifluoromethyl, alkoxy, haloalkoxy, alkylthio, alkylsufinyl and alkylsulfonyl;

$R^1$ is a hydrogen atom, alkyl, or alkoxy;

$R^2$ is a phenyl or cycloalkyl group which is unsubstituted or has a phenyl substituent and wherein the phenyl substituent may have 1 to 5 halogen atoms and/or 1 to 3 alkyl substituents.

2. A composition as claimed in claim 1 where R' is $C[CO_2CH_3]{=}CHCH_3$ or $C[CONHCH_3]{=}NOCH_3$.

3. A composition as claimed in claim 1 which comprises, as active ingredient I, a compound of the following formulae:

4. A composition as claimed in claim 1 which comprises, as the amide compound, a compound of the formula II wherein the radical A is one of the following groups:

pyridin-3-yl which is unsubstituted or substituted in the 2-position by halogen, methyl, difluoromethyl, trifluoromethyl, methoxy, methylthio, methylsufinyl or methylsulfonyl;

thiazol-5-yl which is unsubstituted or substituted in the 2- and/or 4-position by methyl, chlorine, difluoromethyl or trifluoromethyl;

thiazol-5-yl which is unsubstituted or substituted in the 2- and/or 5-position by methyl, chlorine, difluoromethyl or trifluoromethyl;

1-methylpyrazol-4-yl which is unsubstituted or substituted in the 3- and/or 5-position by methyl, chlorine, difluoromethyl or trifluoromethyl; or oxazol-5-yl which is unsubstituted or substituted in the 2- and/or 4-position by methyl or chlorine.

5. A composition as claimed in claim 1 which comprises, as the amide compound, a compound of the formula II where $R^2$ is a phenyl group which is unsubstituted or substituted by the substituent mentioned in claim 1.

6. A composition as claimed in claim 5 where $R^2$ is a phenyl group which has the substituent in the 2-position.

7. A composition as claimed in claim 1 which comprises, as the amide compound, a compound of the formula IIa:

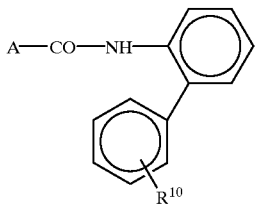

(A2) 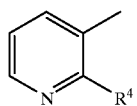

(A5) 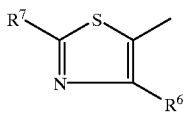

(A6) 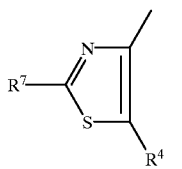

(A7) 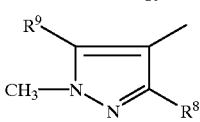

(A8) 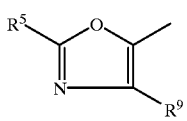

where
R⁴ is trifluoromethyl or chlorine,
R⁶ is methyl, difluoromethyl, trifluoromethyl or chlorine,
R⁷ is hydrogen, methyl or chlorine,
R⁸ is methyl, difluoromethyl or trifluoromethyl,
R⁹ is hydrogen, methyl, difluoromethyl, trifluoromethyl or chlorine, and
R¹⁰ is C₁–C₄ alkyl or halogen.

8. A composition as claimed in claim 1 which comprises, as the amide compound, a compound of the formula IIb.

(IIb) 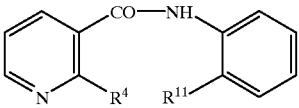

where
R⁴ is halogen and
R¹¹ is phenyl which is substituted by halogen.

9. A composition as claimed in claim 1 which comprises, as the amide compound, a compound of the formulae below:

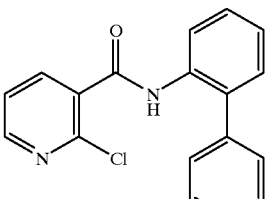

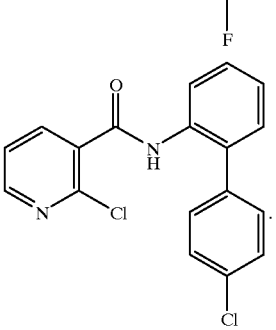

10. A composition as claimed in claim 1 which is conditioned in two parts, one part comprising the active ingredient I in a solid or liquid carrier and the other part comprising the amide compound of the formula II in a solid or liquid carrier.

11. A method of controlling harmful fungi, which comprises treating the fungi, their environment, or the materials, plants, seeds, soils, areas or spaces to be protected against fungal infection, with a composition as claimed in claim 1, it being possible to apply the active ingredients simultaneously, ie. jointly or separately, or in succession.

* * * * *

UNITED STATES PATENT AND TRADEMARK OFFICE
CERTIFICATE OF CORRECTION

PATENT NO.    : 6,169,056 B1  
DATED         : January 2, 2001  
INVENTOR(S)   : Bayer et al.

It is certified that error appears in the above-identified patent and that said Letters Patent is hereby corrected as shown below:

<u>Column 28,</u>  
Line 52, "thiazol-5yl" should be -- thiazol-4-yl --.

Signed and Sealed this

Twenty-fourth Day of December, 2002

JAMES E. ROGAN  
*Director of the United States Patent and Trademark Office*